(12) United States Patent
Chen

(10) Patent No.: US 9,333,367 B2
(45) Date of Patent: *May 10, 2016

(54) CHARGER WITH ORTHOGONAL PCB FOR IMPLANTABLE MEDICAL DEVICE

(71) Applicant: Boston Scientific Neuromodulation Corporation, Valencia, CA (US)

(72) Inventor: Joey Chen, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/674,458

(22) Filed: Mar. 31, 2015

(65) Prior Publication Data

US 2015/0202449 A1 Jul. 23, 2015

Related U.S. Application Data

(62) Division of application No. 11/460,955, filed on Jul. 28, 2006, now Pat. No. 9,002,445.

(51) Int. Cl.
*A61N 1/378* (2006.01)
*A61N 1/372* (2006.01)
*H05K 1/14* (2006.01)
*H05K 3/36* (2006.01)

(52) U.S. Cl.
CPC ............ *A61N 1/3787* (2013.01); *A61N 1/37235* (2013.01); *H05K 1/141* (2013.01); *H05K 3/366* (2013.01)

(58) Field of Classification Search
CPC .................................................... A61N 1/3787
See application file for complete search history.

(56) References Cited

U.S. PATENT DOCUMENTS

| 3,646,940 | A | 3/1972 | Timm et al. ................... 128/421 |
| 3,822,708 | A | 7/1974 | Zilber ........................... 128/419 |
| 4,197,850 | A | 4/1980 | Schulman et al. ............ 128/419 |
| 4,223,679 | A | 9/1980 | Schulman et al. ............ 128/419 |
| 4,231,027 | A | 10/1980 | Mann et al. ................... 340/636 |

(Continued)

FOREIGN PATENT DOCUMENTS

| EP | 0999874 | 9/2004 |
| WO | 98/37926 | 9/1998 |

(Continued)

OTHER PUBLICATIONS

International Preliminary Report on Patentability and Written Opinion regarding corresponding PCT application No. PCT/US2007/065386, dated Feb. 12, 2009.

(Continued)

*Primary Examiner* — Eric D. Bertram
(74) *Attorney, Agent, or Firm* — Lewis, Reese & Nesmith, PLLC

(57) ABSTRACT

An external charger for an implantable medical device, comprises a housing, an alternating current (AC) coil and substrate contained within the housing, and one or more electronic components mounted to the substrate. The AC coil is configured for wirelessly transmitting magnetic charging energy to the implantable medical device. The AC coil is disposed in a first plane, with the magnetic charging energy having a field directed perpendicular to the first plane. At least a portion of the substrate has a surface extending along a second plane that is substantially perpendicular to the first plane.

10 Claims, 9 Drawing Sheets

(56) References Cited

U.S. PATENT DOCUMENTS

| | | | | |
|---|---|---|---|---|
| 4,232,679 | A | 11/1980 | Schulman | 128/419 |
| 4,340,062 | A | 7/1982 | Thompson et al. | 128/419 |
| 4,459,989 | A | 7/1984 | Borkan | 128/421 |
| 4,476,868 | A | 10/1984 | Thompson | 128/419 |
| 4,793,353 | A | 12/1988 | Borkan | 128/421 |
| 5,690,693 | A | 11/1997 | Wang et al. | 607/61 |
| 5,769,877 | A | 6/1998 | Barreras | 607/61 |
| 5,861,019 | A | 1/1999 | Sun et al. | 607/60 |
| 5,948,006 | A | 9/1999 | Mann | 607/61 |
| 6,067,474 | A | 5/2000 | Schulman et al. | 607/57 |
| 6,099,495 | A | 8/2000 | Kinghorn et al. | 604/93 |
| 6,178,353 | B1 * | 1/2001 | Griffith | A61N 1/37223 607/61 |
| 6,185,452 | B1 | 2/2001 | Schulman et al. | 604/20 |
| 6,205,359 | B1 | 3/2001 | Boveja | 607/45 |
| 6,275,737 | B1 | 8/2001 | Mann | 607/61 |
| 6,315,721 | B2 | 11/2001 | Schulman et al. | 600/301 |
| 6,324,431 | B1 | 11/2001 | Zarinetchi et al. | 607/61 |
| 6,327,504 | B1 * | 12/2001 | Dolgin | A61M 1/127 607/61 |
| 6,505,077 | B1 | 1/2003 | Kast et al. | 607/61 |
| 6,516,227 | B1 | 2/2003 | Meadows et al. | 607/46 |
| 6,850,803 | B1 | 2/2005 | Jimenez et al. | 607/61 |
| 6,895,280 | B2 | 5/2005 | Meadows et al. | 607/46 |
| 7,114,502 | B2 | 10/2006 | Schulman et al. | 128/899 |
| 7,496,404 | B2 | 2/2009 | Meadows et al. | 607/46 |
| 9,002,445 | B2 * | 4/2015 | Chen | A61N 1/3787 607/2 |
| 2005/0075696 | A1 | 4/2005 | Forsberg et al. | 607/61 |

FOREIGN PATENT DOCUMENTS

| | | | |
|---|---|---|---|
| WO | 01/83029 | 11/2001 | |
| WO | 01/85250 | 11/2001 | A61N 1/02 |
| WO | 2005/032658 | 4/2005 | A61N 1/378 |
| WO | 2005/037364 | 4/2005 | |
| WO | 2005/037365 | 4/2005 | |
| WO | 2005/039698 | 5/2005 | |
| WO | 2005/042098 | 5/2005 | |

OTHER PUBLICATIONS

Examiner's First Report on corresponding Australian patent application No. 2007276980, dated Jan. 28, 2010.

* cited by examiner

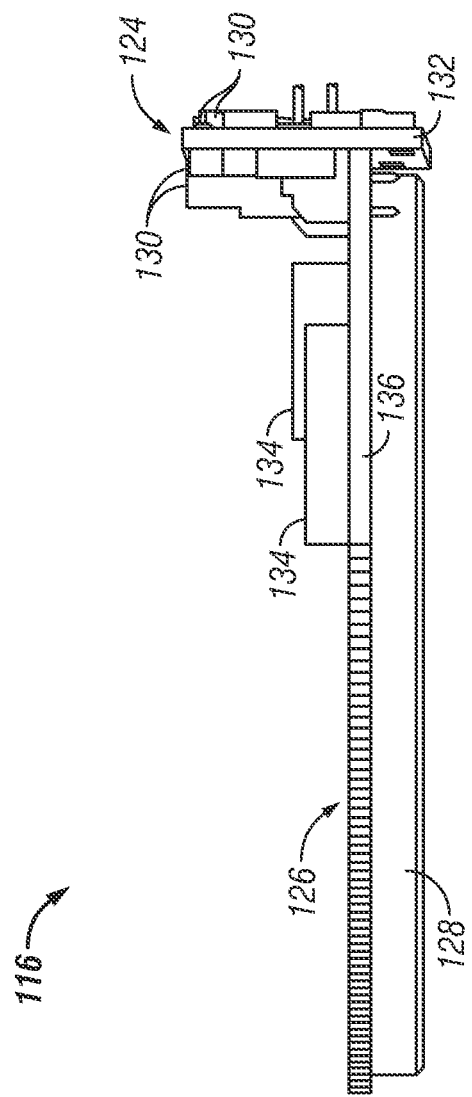

CHARGER WITH ORTHOGONAL PCB FOR IMPLANTABLE MEDICAL DEVICE

CROSS REFERENCE TO RELATED APPLICATIONS

This is a divisional application of U.S. patent application Ser. No. 11/460,955, filed Jul. 28, 2006 (now U.S. Pat. No. 9,002,445), which is incorporated herein by reference and to which priority is claimed.

FIELD OF THE INVENTION

The present invention relates generally to chargers for implantable medical devices, and more particularly, to external chargers for fully implantable medical devices, e.g., pulse generators used in a Spinal Cord Stimulation (SCS) system or other type of neural stimulation system.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a spinal cord stimulation system, such as that disclosed in U.S. Pat. No. 6,516,227 ("the '227 patent"), issued Feb. 4, 2003 in the name of inventors Paul Meadows et al., which is incorporated herein by reference in its entirety.

Spinal cord stimulation is a well-accepted clinical method for reducing pain in certain populations of patients. A spinal cord stimulation (SCS) system typically includes an implantable pulse generator and at least one electrode lead that carries electrodes that are arranged in a desired pattern and spacing to create an electrode array. Individual wires within the electrode lead(s) connect with each electrode in the array. The electrode lead(s) is typically implanted along the dura of the spinal cord, with the electrode lead(s) exiting the spinal column, where it can generally be coupled to one or more electrode lead extensions. The electrode lead extension(s), in turn, are typically tunneled around the torso of the patient to a subcutaneous pocket where the implantable medical device is implanted. Alternatively, the electrode(s) lead may be directly coupled to the implantable pulse generator. For examples of other SCS systems and other stimulation systems, see U.S. Pat. Nos. 3,646,940 and 3,822,708, which are hereby incorporated by reference in their entireties.

Of course, implantable pulse generators are active devices requiring energy for operation. Oftentimes, it is desirable to recharge an implanted pulse generator via an external charger, so that a surgical procedure to replace a power depleted implantable pulse generator can be avoided. To wirelessly convey energy between the external charger and the implanted pulse generator, the charger typically includes an alternating current (AC) charging coil that supplies energy to a similar charging coil located in or on the implantable pulse generator. The energy received by the charging coil located on the implantable pulse generator can then be used to directly power the electronic componentry contained within the pulse generator, or can be stored in a rechargeable battery within the pulse generator, which can then be used to power the electronic componentry on-demand.

FIGS. 1 and 2 illustrate one example of an external charger 10 capable of wirelessly transmitting energy to an implantable pulse generator (not shown) via inductive coupling. The external charger 10 includes an electronic substrate assembly 14 including a printed circuit board (PCB) 16, and an AC charging coil (not shown) mounted to the bottom of the PCB 16, and various electronic components 20, such as microprocessors, integrated circuits, capacitors, audio transducers, connectors, mounted to the top of the PCB 16. The external charger 10 further includes a power source, and in particular a battery 24, electrically coupled to the electronic components 20 via spring terminals 26 mounted to the PCB 16. The pulse generator 10 includes a case 30, which serves to house all of the afore-mentioned components in a suitable manner. The case 30 comprises a bottom half 32 and a top half (not shown) that mate with each other in a clam-shell arrangement to enclose the inner components. The external charger 10 may also include a power on/off button to allow a user to initiate a charging function, status indicators for providing visual and/or audible signals to the user, and recharging terminals (all not shown) to allow the battery 24 to be recharged.

As shown in FIG. 1, electrical current flowing through the AC charging coil induces a magnetic field in a direction perpendicular to the plane in which the charging coil 18 lies. Thus, when a face of the case 30 is oriented in close proximity to an implanted device, such that the AC charging coil 18 is parallel to a corresponding coil within the implanted device, the magnetic field generated by the charging coil 18 induces an electrical current within a corresponding coil to charge a battery within, or otherwise provide power, to the implanted device.

As can be appreciated, the size of the charger 10 is dictated, at least in part, by the power efficiency of the AC charging coil. Due to the close proximity between the electronic components 20 and associated circuit traces on the PCB 16 and the charging coil 28, the magnetic field generated by the charging coil 18 induces eddy currents on the surface of the PCB 18 and components 20. Eddy currents are undesirable because they transform magnetic energy into thermal energy, thereby reducing the power efficiency of the AC charging coil, as well as undesirably heating the electronic components 20. In addition, the eddy currents create noise within the signals generated within the electronic components 20.

There, thus, remains a need to provide a more power efficient external charger for an implantable medical device.

SUMMARY

In accordance with the present invention, an external charger for an implantable medical device is provided. In one embodiment, the implantable medical device is an implantable pulse generator (IPG) for delivering stimulation energy to a patient's spinal cord for the treatment of pain. It is noted that the present invention may be used with similar electrical stimulators and/or electrical sensors that may be used as a component of numerous different types of stimulation systems. For example, the present invention may be used as part of a pacemaker, a defibrillator, a cochlear stimulator, a retinal stimulator, a stimulator configured to produce coordinated limb movement, a cortical and deep brain stimulator, or in any other neural stimulator configured to treat urinary incontinence, sleep apnea, shoulder sublaxation, etc. The present invention may also be used with non-electrical implantable therapy systems, such as with drug pumps. Although the present invention lends itself well to therapy systems, which typically include implantable medical devices that require a considerable amount of energy to operate, it is to be understood that the invention is not limited to its use with implantable therapy systems. Rather, the present invention may be used with any type of implantable medical device used to perform a medical function within a patient, whether therapeutic and/or diagnostic The external charger comprises a housing, and an alternating (AC) coil disposed in a first plane within the housing. The AC coil is configured for wirelessly transmitting magnetic charging energy to the implantable medical device. The external charger further comprises one or more electronic components contained within the housing. In one embodiment, the electronic component(s) perform a signal processing function. The external charger may further comprise an energy source contained within the housing, wherein the charging energy is derived from the energy source. The external charger may optionally be incorporated into a tissue implantable system having the implantable medical device. In this case, the implantable medical device includes a rechargeable energy source and circuitry configured for charging the energy source in response to wirelessly receiving the magnetic charging energy from the external charger.

In accordance with a first aspect of the present invention, at least one electronic component comprises a plurality of electronic components arranged along a second plane that is substantially perpendicular to the first plane. Although the present inventions should not be limited in their broadest aspects, the distribution of the electronic components within a plane perpendicular to the plane of the AC coil, in turn, may cause the surfaces of the electronic components to be parallel to the magnetic field generated by the AC coil, thereby minimizing the eddy currents created on the electronic components.

In accordance with a second aspect of the present invention, the external charger further comprises a substrate (e.g., a printed circuit board (PCB)) on which the electronic component(s) are mounted. At least a portion of the substrate has a surface extending along a second plane substantially perpendicular to the first plane in which the AC coil is disposed. In one embodiment, the entire portion of the substrate has a surface that extends along the second plane. In one embodiment, Although the present inventions should not be limited in their broadest aspects, the disposition of the substrate within a plane perpendicular to the plane of the AC coil, in turn, may cause the surface of the substrate to be parallel to the magnetic field generated by the AC coil, thereby minimizing the eddy currents created on any metallic elements on the substrate, as well as the electronic component(s). In an optional embodiment, the external charger comprises another substrate having a surface extending along a third plane substantially parallel to the first plane, and one or more additional electronic components mounted to the surface of the other substrate.

In accordance with a third aspect of the present invention, at least a portion of the substrate has a surface that does not necessarily extend along a second plane that is substantially perpendicular to the first plane in which the AC coil is disposed. Rather, at least a portion of the substrate may have a surface extending along a second plane in a non-parallel relationship with the first plane, which second plane may, e.g., form an angle with the first plane equal to or greater than forty-five degrees.

Other and further aspects and features of the invention will be evident from reading the following detailed description of the preferred embodiments, which are intended to illustrate, not limit, the present inventions.

BRIEF DESCRIPTION OF THE DRAWINGS

The above and other aspects of the present invention will be more apparent from the following more particular description thereof, presented in conjunction with the following drawings. The drawings illustrate the design and utility of embodiments of the present invention, in which similar elements are referred to by common reference numerals. In order to better appreciate how the above-recited and other advantages of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 9 is a rear perspective view of the electronic assembly of FIG. 7.

DETAILED DESCRIPTION

Figure 1:
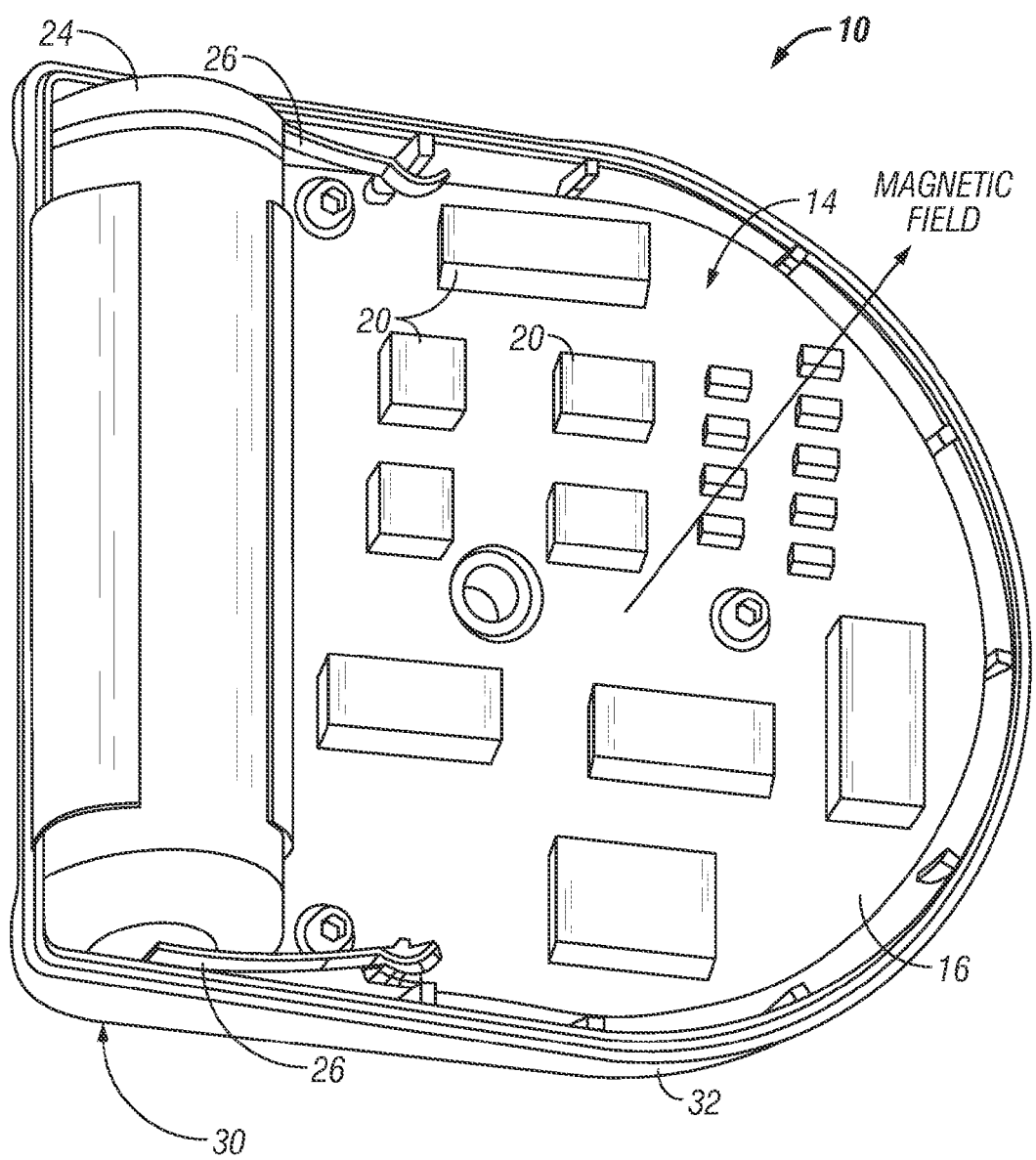
FIG. 1 shows a perspective of a prior art external charger for an implantable medical device.
Figure 2:
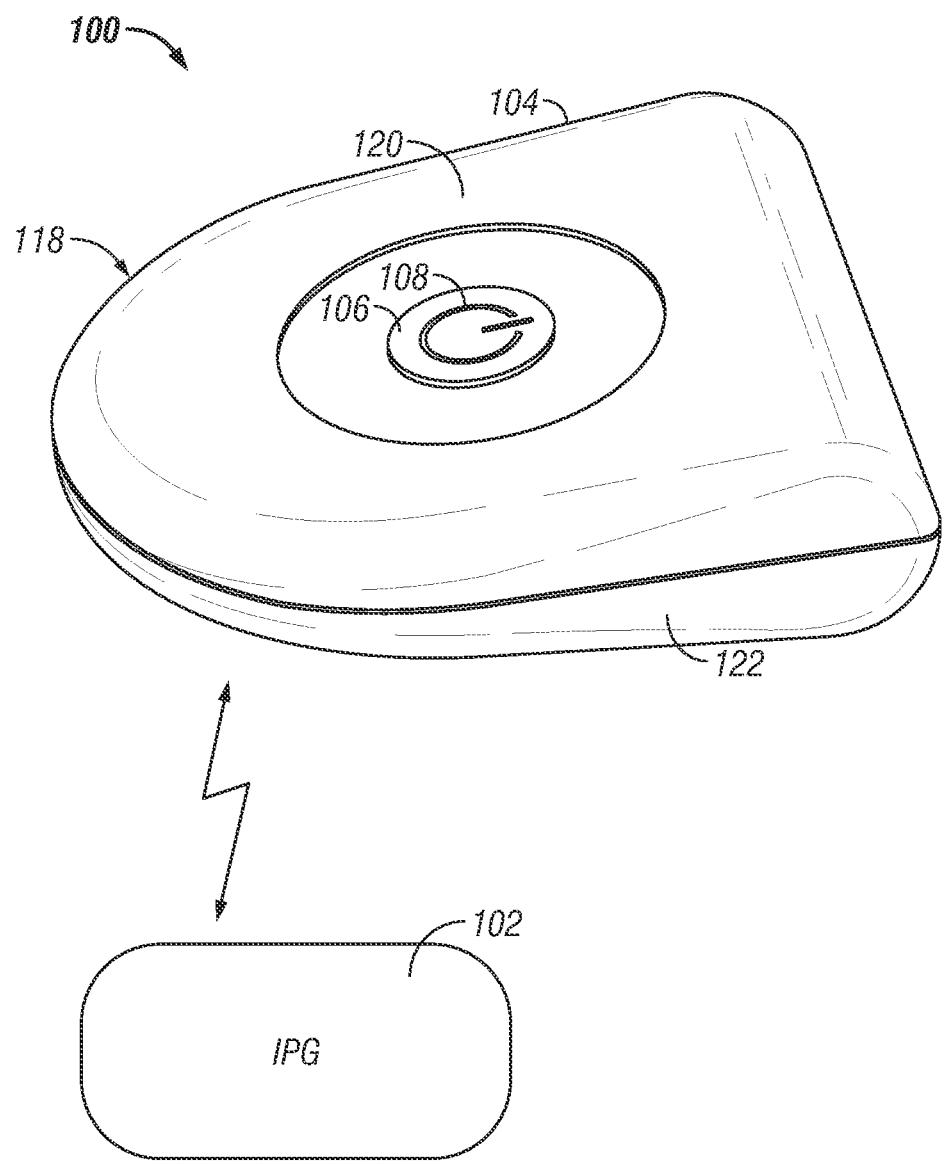
FIG. 2 shows a top perspective view of an external charger for an implantable device constructed in accordance with one embodiment of the present invention.

Turning first to FIG. 2, one embodiment of an implantable system 100 constructed in accordance with the present inventions will now be described. The implantable system 100 generally comprises an implantable medical device 102, such as an IPG, and an external charger 104. In the illustrated embodiment, the IPG 102 is coupled to one or more electrical stimulation leads (not shown) that can be implanted within the epidural space as part of a spinal cord stimulation (SCS) system for the treatment of chronic pain.

The charger 104 is configured for transcutaneously charging the IPG 102 via inductive coupling. In particular, the charger 104 provides time varying magnetic energy, which is received by the IPG 102. A corresponding pick-up coil (not shown) within the IPG 102 transforms the magnetic energy into an electrical current, which is used by circuitry to charge a battery (not shown) within the IPG 102.

In the illustrated embodiment, the charger 104 is a portable device that can be held in one hand. For example, the charger 104 may have a maximum width (i.e., the dimension that would span the palm of a hand) that is less than 3 inches and may be light enough so that it is comfortable and easy to wear for an extended period of time. The charger 104 outputs enough power (e.g., 1-2 W) to charge the battery of the IPG 102 from complete or near-complete discharge to end of charge in reasonable period of time, e.g., four hours +/− one hour. The charger 104 is also capable of fully charging the battery of the IPG 102 at reasonable implant depths. For example, the charger 104 may be in charging distance of the IPG 102 if the bottom surface of the charger 104 is separated less than 2.5 cm from the top surface of the IPG 102 along a vertical axis.

The charger 104 includes a power on/off button 106 for providing a means for alternately turning the charger 104 on and off, and an indicator light 108 and internal audio transducer 110 (shown in FIGS. 6 and 7) for indicating the status of the charger 104. The power button 106 may take the form of a momentary-contact membrane dome switch for power on/off, and the indicator light 108 may take the form of a bi-colored light emitting diode (LED). In the illustrated embodiment, the indicator light 108 is integrated with the power button 106. When the charger 104 is initially turned on, the indicator light 108 will turn green or amber and the audio transducer 110 will provide a short audible tone.

The charger 104 will then begin wirelessly transmitting magnetic energy, while searching for the IPG 102. The audio transducer 110 will provide an intermittent audible sound when the charger 104 is out-of-range or misaligned with respect to the IPG 102, and will stop providing the audible sound when the charger 104 is in-range and aligned with respect to the IPG 102, at which point the charger 104 may be held in place over the IPG 102 by using double-side adhesive pads or a belt. If the charger 104 becomes out-of-range or misaligned with respect to the IPG 102, the audio transducer 110 will again generate the audible signal, so that the position of the charger 104 relative to the IPG 102 can be readjusted. A back-telemetry link from the IPG 102 may communicate to the charger 104 when the IPG battery is fully charged. If this occurs or if the charger is fully discharged, the charger 104 may automatically shut down. The audio transducer 110 may generate an audible signal that indicates when the IPG battery is fully charged.

Figure 3:
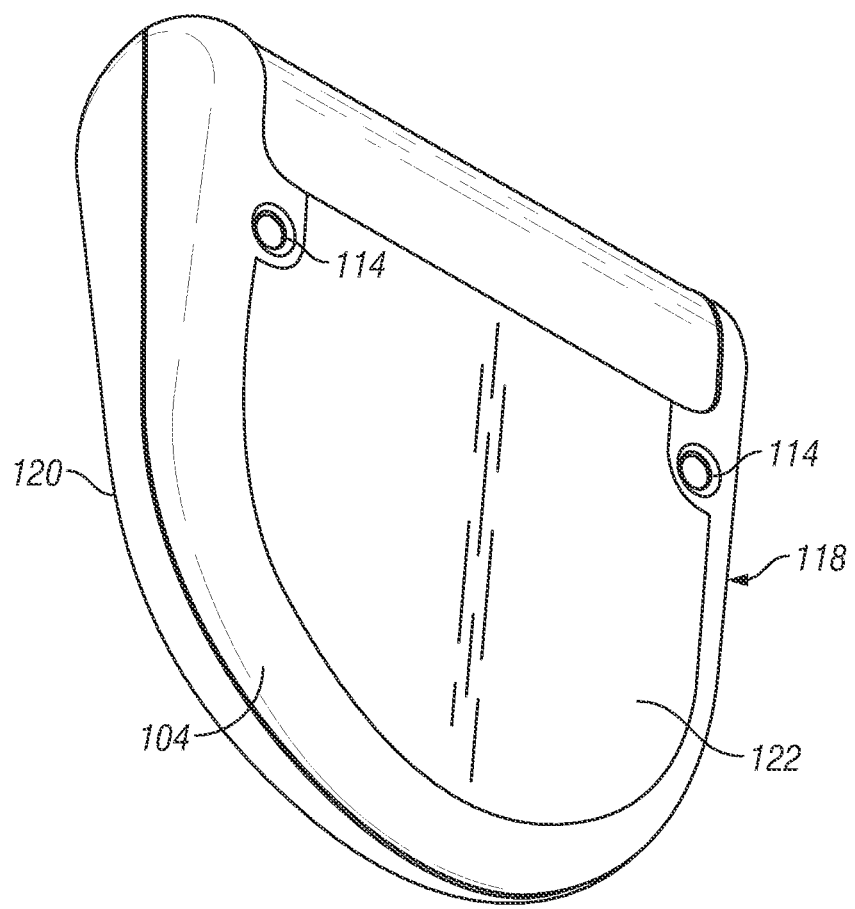
FIG. 3 shows a bottom perspective view of the external charger of FIG. 1.
Figure 5:
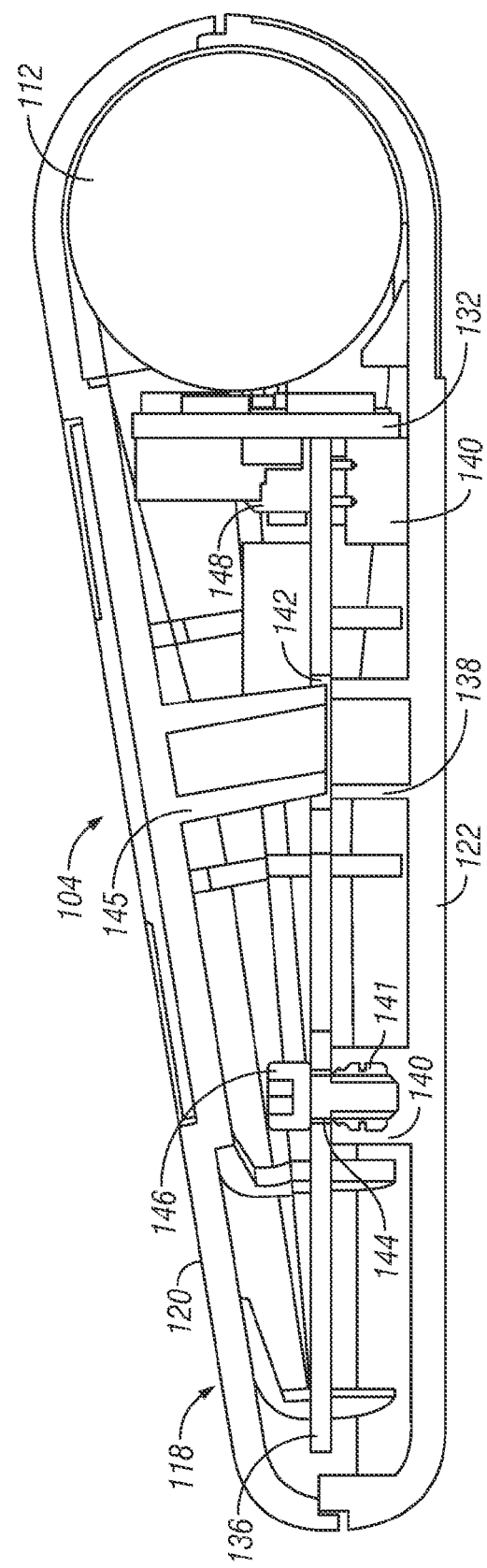
FIG. 5 is a cross-section view of the external charger of FIG. 1.
Figure 6:
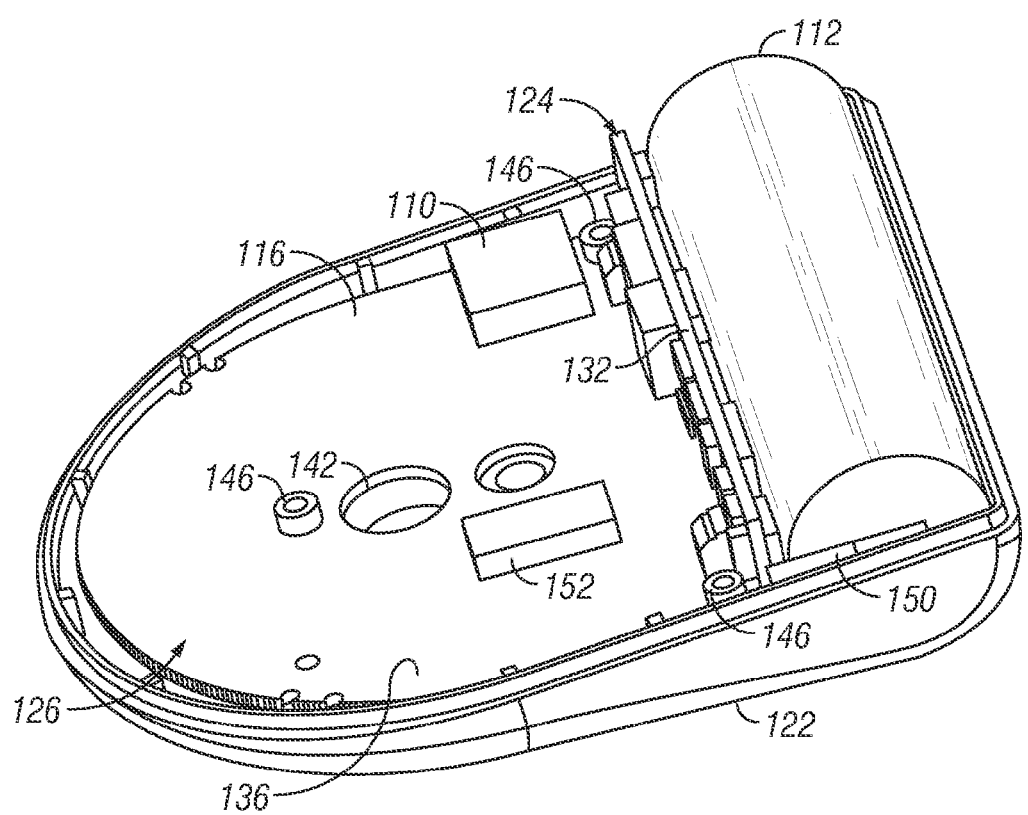
FIG. 6 is a front-top perspective view of the external charger of FIG. 1, particularly showing the top housing half removed.
Figure 7:
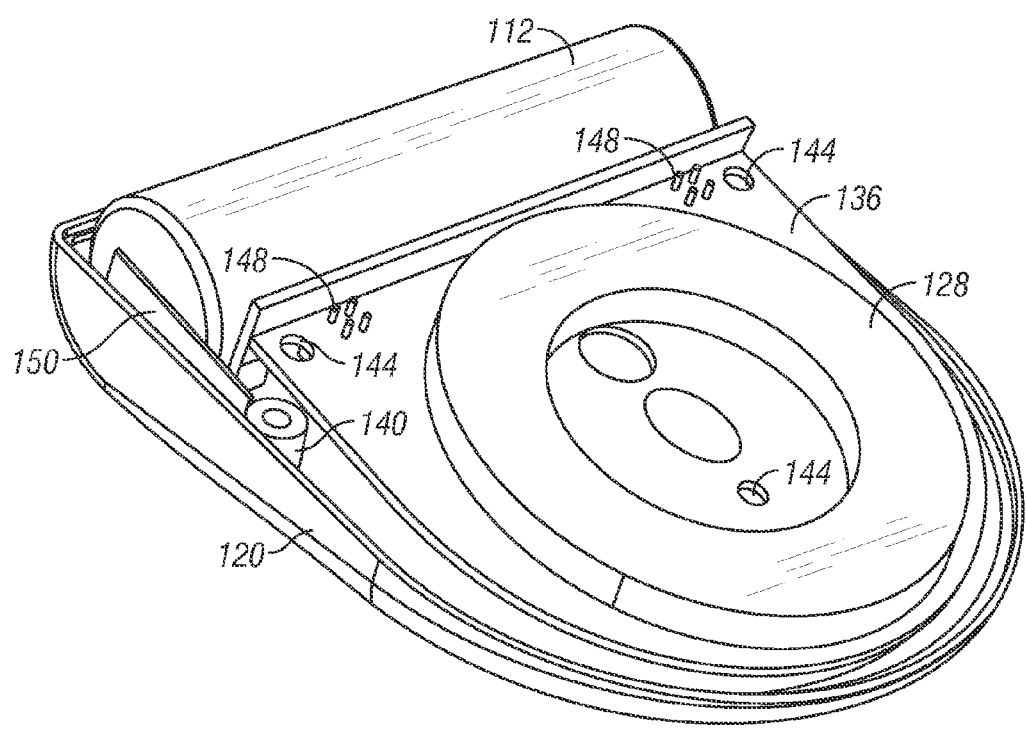
FIG. 7 is a front-rear perspective view of the external charger of FIG. 1, particularly showing the bottom housing half removed.

In the illustrated embodiment, the charger 104, itself, is rechargeable, and thus, includes a rechargeable battery 112 (shown in FIGS. 5 and 6). The audio transducer 110 may generate a tone when the battery 112 is depleted to indicate to the user that the charger 104, itself, needs to be recharged. In this case, the charger 104 may be placed into a cradle of a DC charger base station (not shown) until fully charged. To this end, as shown in FIG. 3, the charger 104 includes a pair of electrical contacts 114 for connection to corresponding electrical contacts on the charger base station. The indicator light 108 may turn green to indicate to the user when the charger 104 has been fully charged.

Referring further to FIGS. 4-9, the inner components of the charger 104 will now be described. The charger 104 generally includes an electronic assembly 116 and a housing 118 for containing the electronic assembly 116. The housing 118 has a clam-shell arrangement that includes a top half 120 and a bottom half 122, which are suitably coupled together, e.g., using a snap-fit interference arrangement, to enclose the electronic assembly 116 within the housing 118. The electronic assembly 116 includes a vertical printed circuit board (PCB) assembly 124, a horizontal printed circuit board (PCB) assembly 126, an alternating current (AC) charging coil 128 (best shown in FIGS. 4 and 7)(AC coil 128 not shown in FIG. 5 to better illustrate other components) disposed on the bottom surface of the horizontal PCB assembly 126, and a power source, and in particular, the rechargeable battery 112.

The vertical PCB assembly 124 comprises control and signal processing circuitry 130 and a printed circuit board (PCB) 132 for carrying the circuitry 130. The horizontal PCB assembly 126 comprises additional electronic circuitry 134 and a printed circuit board (PCB) 136 for carrying the circuitry 134. The PCBs 132, 136 are standard PCBs composed of a rigid, non-conductive, substrate on which conductive pathways or traces are etched or laminated onto the substrate. Alternatively, the electronic circuitry 130, 134 may be mounted on flex circuits, ceramic boards, wire-wrapped boards, or any other non-conductive substrate on which the electronic circuitry 130, 134 may be mounted in a plane.

Figure 8:
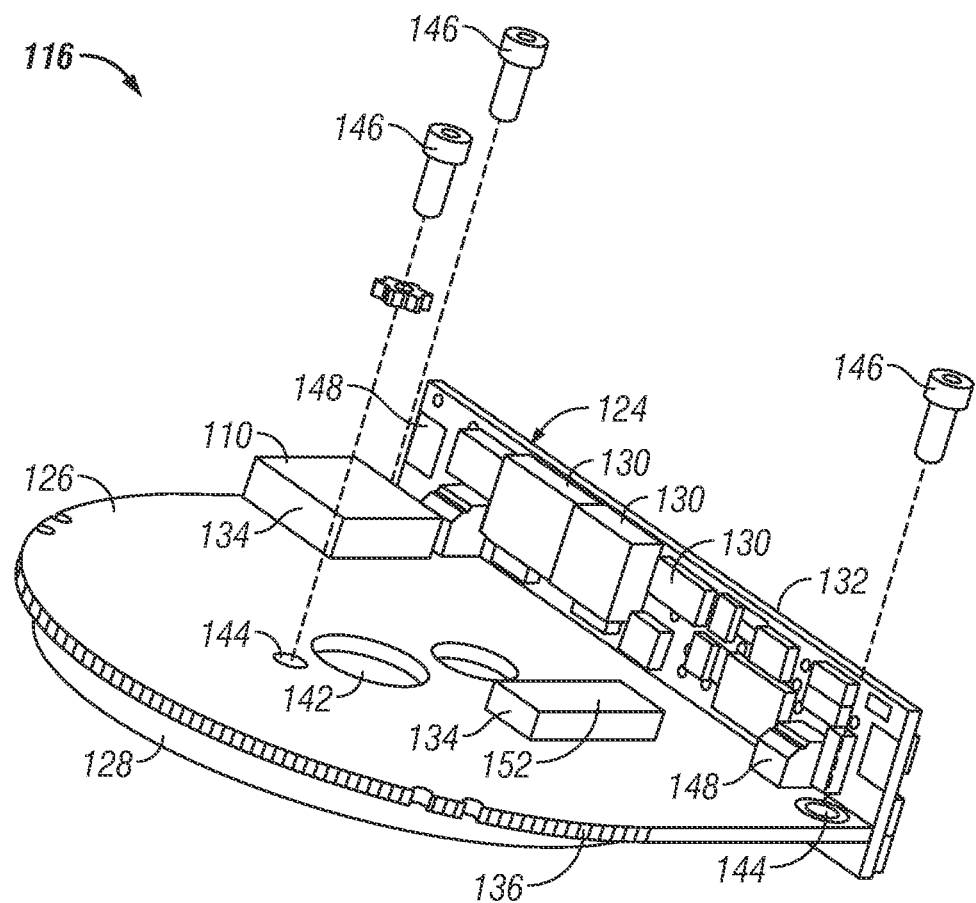
FIG. 8 is a front perspective view of an electronic assembly contained within the external charger of FIG. 1.

The horizontal PCB assembly 126 is suitably mounted to the bottom housing half 122. The bottom housing half 122 has four bosses, a center one 138 of which extends within an aperture 142 within the center of the PCB 136 when the horizontal PCB assembly 126 is placed within the bottom housing half 122, and the remaining three 140 (only one shown) of which include threaded inserts 141 that receive respective screws 146 extending through apertures 144 located on the PCB 136. The top housing half 120 has a boss 145 that extends within the aperture 142 within the PCB 136 opposite the center boss 138 of the bottom housing half 122, as best shown in FIG. 5. The vertical PCB assembly 124 is mounted to the horizontal PCB assembly 126, such that the surface of the vertical PCB 132 is perpendicular to the surface of the horizontal PCB 136. As best shown in FIG. 8, the vertical PCB assembly 124 is electrically coupled to the vertical PCB assembly 126 via angled pin blocks 148. The angled pin blocks 148 also facilitate the mechanically coupling between the respective PCBs 132, 136.

The vertical PCB 132 includes a pair of positive and negative spring terminals 150 (only one shown in FIG. 6) between which the battery 112 is coupled, thereby electrically coupling the battery 112 to the vertical PCB assembly 124. The rechargeable battery 112 can take the form of any battery that can be repeatedly recharged without substantially reducing the capacity of the battery, e.g., lithium cylindrical battery. Alternatively, other types of rechargeable batteries can be used. Alternatively, the charger 104 may not be rechargeable, in which case, the power source within the charger 104, can take the form of a standard replaceable battery. In any event, the battery 112 provides a source of electrical energy for the charging coil 128, which transforms the electrical energy into the magnetic energy that inductively charges the IPG battery. The battery 112 also provides a source of energy for the electronic circuitry 130 carried by the vertical PCB 132.

The charging coil 128 may be any suitable coil capable of creating a magnetic field in response to the flow of electrical current through the coil, but in the illustrated embodiments, takes the form of a multi-filament copper coil having a sufficient number of windings. The charging coil 128 may be formed by wrapping a copper wire around a mandrel, and then removing the mandrel to create an air-core coil. The charging coil 128 is mounted to the bottom surface of the horizontal PCB 136 using suitable means, such as bonding. The terminal ends of the charging coil 128 are soldered to the horizontal PCB 132 to electrical connect the charging coil 128 to the vertical PCB assembly 124.

The electronic circuitry 130 mounted on the vertical PCB 132 includes an amplifier for amplifying current from the battery 112, and an oscillator for providing alternating current to the charging coil 128, which induces a time varying magnetic field in a direction perpendicular to the plane in which the coil 128 lies. The electronic circuitry 130 also includes telemetry circuitry for communicating with the IPG 102 (e.g., to determine distance between the charger 104 and the IPG 102, or to obtain battery level from IPG 102) via the AC charging coil 128, status circuitry for controlling the visual and audible signals emitted by the visual indicator 108 and audio transducer 110, and temperature sensing circuitry for sensing the temperature of the charger 104 via a thermistor (not shown) to ensure that the charger 104 does not overheat and cause burns to the patient.

The electronic circuitry 130 also includes charging circuitry for charging the battery 112 and safety circuitry for ensuring that the battery 112 is not overcharged. To this end, the bosses 140 along the lateral sides of the charger 104 (only one lateral boss 140 shown in FIG. 5) are located opposite the electrical contacts 114, and the threaded inserts within the bosses 140 provide an electrical connection between the electrical contacts 114 and the horizontal PCB assembly 126, which is in turn, in electrical contact with the vertical PCB assembly 124 via the pin blocks 148, so that the charging circuitry may receive the recharging energy when the charger 104 is placed within the cradle of the charger base station.

Figure 4:
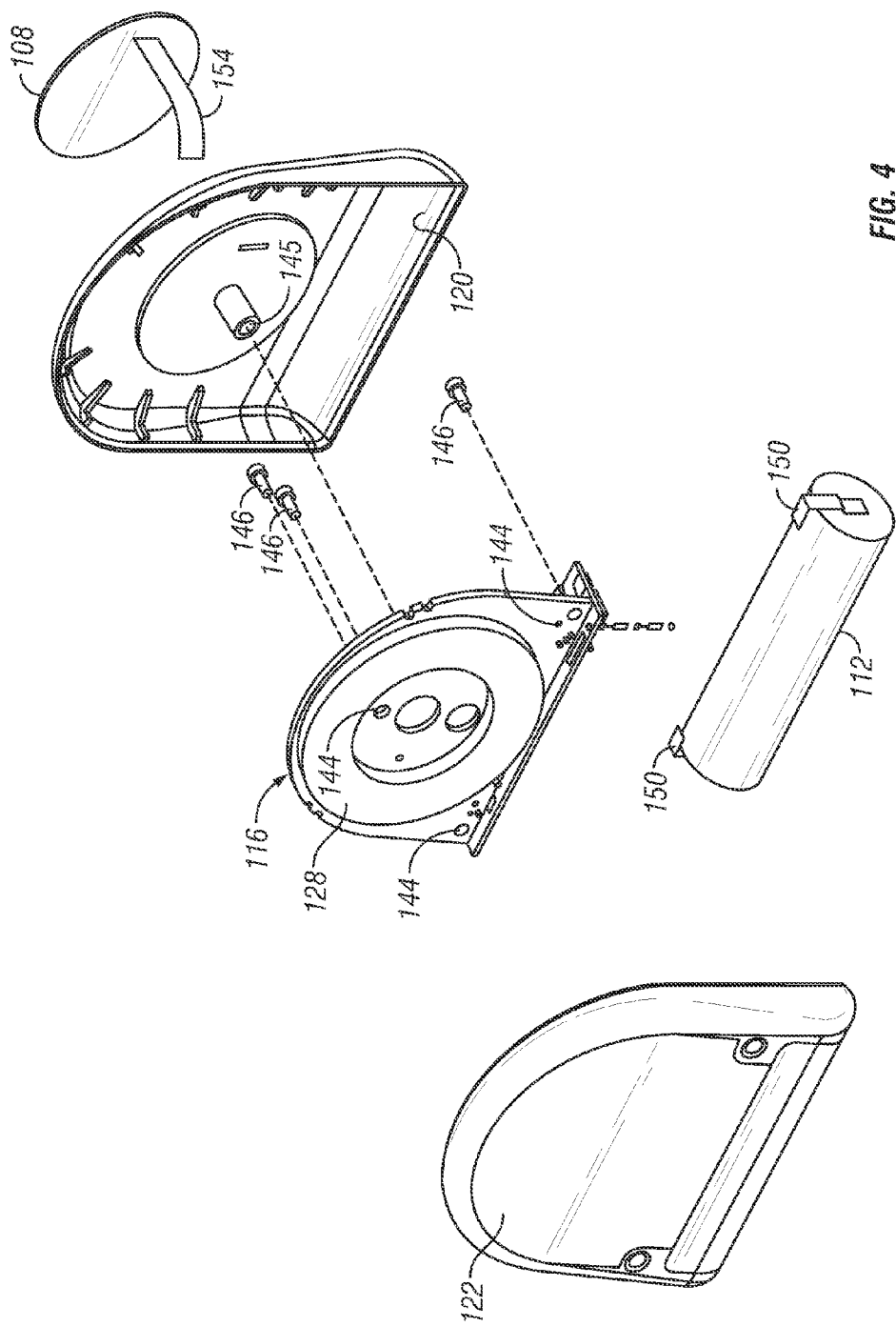
FIG. 4 shows an exploded perspective view of the external charger of FIG. 1.

The electronic circuitry 134 mounted on the horizontal PCB 136 includes a connector 152 to which the power button 106 is operably connected to via a ribbon cable 154 (shown in FIG. 4). The electronic circuitry 134 also includes the previously described audio transducer 112. The connector 152 and audio transducer 110 are electrically coupled to the vertical PCB assembly 124 via the respective pin blocks 148, so that signals can be sent between the vertical PCB assembly 124 and the power on/off button 106, visual indicator 108, and audio transducer 110.

As can be seen, the vertical PCB 132 extends along a plane that is perpendicular to the plane in which the charging coil 128 is disposed. In this manner, the direction of the magnetic field induced by the charging coil 128 is parallel to the plane of the vertical PCB 132, thereby reducing, if not otherwise eliminating, the creation of eddy currents on the vertical PCB 132 and associated electronic circuitry 126. As a result, the efficiency of the charging coil 128 is increased, and the noise and heat otherwise generated by the eddy currents is minimized.

In contrast, the horizontal PCB 136 extends along a plane that is parallel to the plane in which the charging coil 128 is disposed. As a result, the direction of the magnetic field induced by the charging coil 128 is perpendicular to the plane of the horizontal PCB 136 and the associated electronic circuitry 134. While the eddy currents will be induced on the surface of the horizontal PCB 136, the vast majority of the electronic components are mounted to the vertical PCB 132. Thus, because of the reduced number of electronic components and associated electrical traces on the horizontal PCB 136, the eddy currents induced on the horizontal PCB 136 will be minimized. In addition, as shown in FIG. 9, the use of a vertical PCB 132 has the additional advantage of providing a rear surface on which the electronic circuitry 130 can be mounted. In contrast, because the charging coil 128 is mounted on the rear surface of the horizontal PCB 136, there is a limited space on the rear surface of the horizontal PCB 136 to mount additional electronic circuitry. In addition, because the vertical PCB 132 is set back from the charging coil 128, any adverse electrical effects that the electronic circuitry 130 on the vertical PCB 132 is further reduced.

While the charger 104 is described as having two separate and distinct PCBs; i.e., the vertical PCB 132 and the horizontal PCB 136, it should be appreciated that a single PCB having a horizontal and vertical extensions on which the electronic circuitry 130 and 134 is mounted can be used. Alternatively, a horizontal PCB 136 or horizontal extension is not used, in which case, the charger 104 will only have a vertical PCB 132 on which the electronic circuitry 130, 134 is mounted. However, because the horizontal PCB 136 provides a convenient means for properly positioning the connector 152 relative to the power button 106, as well as a convenient means for mounting the charging coil 128 and the entire vertical PCB assembly 124 within the bottom housing half 122, the use of a horizontal PCB 136 or horizontal extension is preferred.

Also, while the use of a vertical PCB 132 minimizes the induction of eddy currents thereon, a PCB that extends along a plane different from a vertical plane can be used. For example, a PCB that is oriented at a 45 degree angle to the plane in which the charging coil 128 is disposed can be used to minimize the induction of eddy currents thereon. The significance is that the closer the plane in which the electronic circuitry is distributed is to being parallel to the magnetic field induced by the charging coil, the less the magnitude of the eddy currents created in the electronic circuitry and associated PCB traces.

It should also be appreciated that, although the distribution of electronic circuitry along a plane perpendicular to the plane in which a charging coil is disposed lends itself well to external chargers for implantable medical devices, the same concept can be incorporated into any implantable medical device (e.g., the IPG 102) where it is desirable to minimize or eliminate eddy currents resulting from a recharging function.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An external charger for an implantable medical device, comprising:
    a housing;
    an alternating current (AC) coil disposed within a first plane within the housing, the AC coil configured for wirelessly transmitting magnetic charging energy to the implantable medical device;
    a substrate contained within the housing, at least a portion of the substrate having a surface extending along a second plane in a non-parallel relationship with the first plane; and
    one or more electronic components mounted to the surface of the substrate,
    wherein the at least a portion of the substrate is located outside of an area within a perimeter of the coil projected in directions perpendicular to the first plane.

2. The external charger of claim 1, wherein the second plane forms an angle with the first plane equal to or greater than forty-five degrees.

3. The external charger of claim 1, wherein the second plane is perpendicular to the first plane.

4. The external charger of claim 1, wherein the substrate comprises a printed circuit board (PCB).

5. The external charger of claim 1, further comprising an energy source contained within the housing, wherein the charging energy is derived from the energy source.

6. The external charger of claim 1, wherein the one or more electronic components perform a signal processing function.

7. The external charger of claim 1, wherein the entirety of the substrate extends along the second plane.

8. An external charger for an implantable medical device, comprising:
- a housing;
- an alternating current (AC) coil disposed in a first plane within the housing, the AC coil configured for wirelessly transmitting magnetic charging energy to the implantable medical device; and
- a plurality of electronic components contained within the housing, the plurality of components arranged along a second plane that is substantially perpendicular to the first plane wherein at least a portion of the plurality of electronic components is located outside of an area within a perimeter of the coil projected in directions perpendicular to the first plane.

9. The external charger of claim 8, further comprising an energy source contained within the housing, wherein the charging energy is derived from the energy source.

10. The external charger of claim 8, wherein the plurality of components is configured for performing one or more signal processing functions.

* * * * *